United States Patent [19]
Nanjo

[11] Patent Number: 5,668,621
[45] Date of Patent: Sep. 16, 1997

US005668621A

[54] HAND-HELD FUNDUS CAMERA WITH SHARED LIGHT PATH

[75] Inventor: Tsuguo Nanjo, Toyohashi, Japan

[73] Assignee: Nidek Company, Ltd., Japan

[21] Appl. No.: 639,551

[22] Filed: Apr. 29, 1996

[30] Foreign Application Priority Data

Apr. 28, 1995 [JP] Japan ................................. 7-129496

[51] Int. Cl.$^6$ ........................................................ A61B 3/10
[52] U.S. Cl. ........................ 351/206; 351/211; 351/221; 396/18
[58] Field of Search ................................. 351/206, 205, 351/211, 221, 208; 354/62

[56] References Cited

U.S. PATENT DOCUMENTS

| | | | |
|---|---|---|---|
| 4,196,979 | 4/1980 | Kohayakawa et al. | 351/7 |
| 4,253,743 | 3/1981 | Matsumura | 351/206 |
| 5,048,946 | 9/1991 | Sklar et al. | 351/206 |
| 5,240,006 | 8/1993 | Fuji et al. | 128/665 |
| 5,308,919 | 5/1994 | Minnich | 128/633 |
| 5,341,180 | 8/1994 | Isogai et al. | 351/206 |
| 5,543,865 | 8/1996 | Nanjo | 351/206 |

FOREIGN PATENT DOCUMENTS 56-63329  5/1981  Japan .

Primary Examiner—Hung X. Dang
Attorney, Agent, or Firm—Rossi & Associates

[57] ABSTRACT

A fundus camera which may maintain sufficient working distance to an eye to be examined, providing a first illumination optical system for illuminating an eye to be examined by using infrared light, a second illumination optical system for illuminating the eye to be examined by using visible light for photo-imaging with part of light path being shared with that of the first illumination optical system an alignment index projection optical system for projecting an alignment index for the adjustment of working distance onto an cornea of the eye to be examined, an observation optical system having photoelectric imaging elements for observing the images of the focusing of the alignment index image and the fundus of the eye to be examined, a first display device for displaying images formed by the photoelectric imaging elements of the observation optical system, a photographing optical system having photoelectric imaging elements for forming images of the fundus of the eye to be examined with part of light path being shared with that of the observation optical system, and a beam splitter disposed along with the light path shared by the photographing optical system and the observation optical system for reflecting the illumination light into the eye to be examined, the suitability of the alignment being determined by observing the images of the focusing of the alignment index image on the first display device.

6 Claims, 3 Drawing Sheets

HAND-HELD FUNDUS CAMERA WITH SHARED LIGHT PATH

BACKGROUND OF THE INVENTION

1. Field of the Invention

The present invention relates to a fundus camera, more particularly to a handheld apparatus for fundoscopic photo-imaging, particularly suitable for lying patients, newborns and children, animals, and handicapped persons.

2. Description of the Related Art

There was proposed two types of illumination system for the conventional handheld fundus cameras.

One is the separate illumination type, having illumination system in which a small prism is positioned slightly below the imaging light axis between the objective lens in the photo-imaging system and the eye of a patient for illuminating the eye transversally upwardly from the bottom side, for separating the illumination system from the photo-imaging system.

The other is the coaxial illumination type, in which half-mirror is placed between the objective lens of the photo-imaging system and the eye for achieving illumination with the axis of the illumination system positioned coaxially with that of the photo-imaging system.

The separate illumination type has advantages that the optical system is simple and a sufficient amount of reflected light may be obtained to achieve compact illumination. However it has a problem that the working range is very short. That is, short working range between the eye and the apparatus may lead to cause patients to feel danger and/or constraint to affect to examination by repetitive blinking and/or distractive eye movement.

On the other hand, the coaxial illumination type has advantages that the working range of the optical system may be elongated as compared with the separate illumination type. However, there is loss of light to decrease the amount of light approximately one quarter so that in case of fundus cameras the illuminating light source has to be powered up and the size thereof has to be grown to achieve sufficient amount of light required.

In both types of illumination, the only way for determining the working distance from the camera to the eye in practice is to collimate illumination light into the anterior of the eye for confirmation, then starting aligning the camera with the eye while observing the light bundle from one side, then looking into the observation through eyepiece by holding the camera so as to maintain the positional relationship with the eye to fine tune of the camera position (incoming illumination, site of imaging, etc.) by finding the fundus image on the view screen. Thus the way of photo-imaging with a handheld camera was relatively instable. As the former type in particular is required to be closer (working distance 5 mm with view angle 30°), this procedure is necessary for ensuring the safety. Even the latter type which is to be farther (working distance 10 mm for view angle 30°), similar procedure is allowed when the operator feels anxiety to keep safety.

Furthermore, as conventional handheld fundus cameras used intensive visible light to be introduced into the fundus for alignment, the subject had to tolerate the introduced illumination light. The situation was undesirable particularly for the lying patients, newborns and children, and animals.

SUMMERY OF THE INVENTION

The present invention has been made in view of the above circumstances and has an object to overcome the above problems, and to provide a fundus camera which may ensure sufficient working distance to the eye being examined as a handheld type.

Another object of the present invention is to provide a fundus camera which may stably shoot photo images, and which allows the suitability of working distance and the confirmation of light axis to be performed easily.

Still another object of the present invention is to provide a fundus camera which allows less tolerance to be imposed to the eye for which a handheld camera is frequently used, such as that of lying patients, newborns and children, animals, and handicapped persons.

According to one aspect of the present invention, there is provided a fundus camera which may maintain sufficient working distance to an eye to be examined, comprising a first illumination optical system for illuminating an eye to be examined by using infrared light, a second illumination optical system for illuminating the eye to be examined by using visible light for photo-imaging, with part of light path being shared with that of the first illumination optical system, an alignment index projection optical system for projecting an alignment index for the adjustment of working distance onto an cornea of the eye to be examined, an observation optical system having photoelectric imaging elements for observing the images of the focusing of the alignment index image and the fundus of the eye to be examined, a first display means for displaying images formed by the photoelectric imaging elements of the observation optical system, a photographing optical system having photoelectric imaging elements for forming images of the fundus of the eye to be examined with part of light path being shared with that of the observation optical system, and a beam splitter disposed along with the light path shared by the photographing optical system and the observation optical system for reflecting the illumination light into the eye to be examined, the suitability of the alignment being determined by observing the images of the focusing of the alignment index image on the first display means.

According to the above constitution, a fundus camera may be achieved in which the amount of illumination light beam required for photo-imaging may be obtained without expanding the size of illumination system, also sufficient working distance to an eye to be examined as a handheld type may be ensured.

In addition, in the fundus camera of handheld type, as the suitability of the alignment and of the working distance in particular may be readily confirmed by observing images through the observation, the operability of the apparatus may be improved, therefore a fundus camera may be achieved which may provide imaging in a stable manner.

Furthermore, by employing invisible illumination light for alignment, the burden is allowed to be significantly decreased, for eyes of subjects such as lying patients, newborns and children, animals, and handicapped persons in particular, for whom a handheld type is especially frequently used.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In drawings.

DETAILED DESCRIPTION OF THE PREFERRED EMBODIMENT

One preferred embodiment according to the present invention will be now described with reference to the accompanying drawings.

Figure 1:
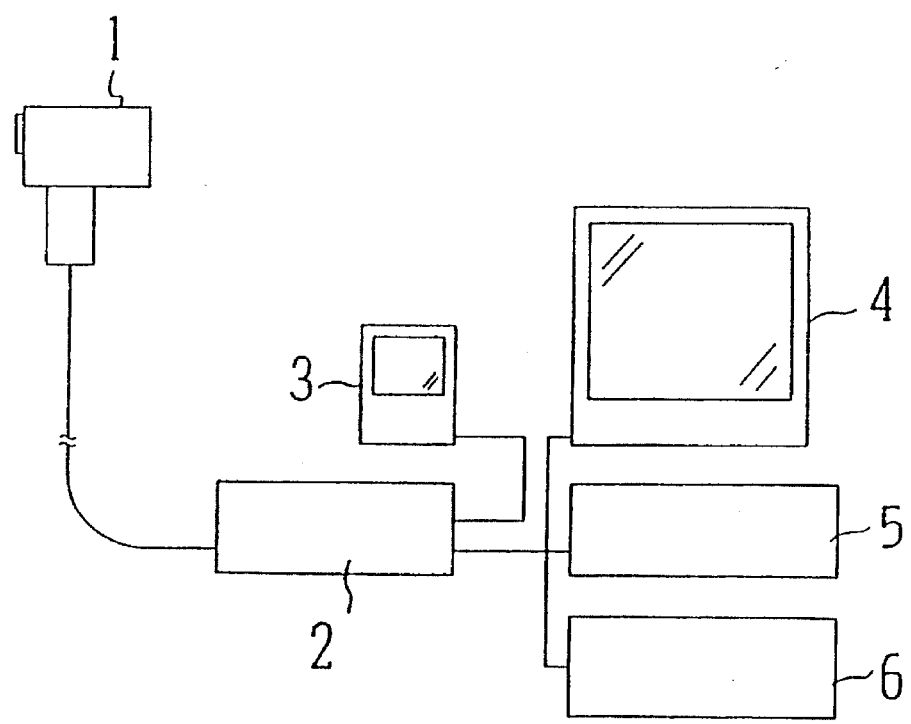
FIG. 1 shows an overview of an apparatus of a preferred embodiment according to the present invention.

FIG. 1 shows an overview of an apparatus according to one embodiment of the present embodiment. The apparatus of the present embodiment comprises a camera 1 enclosing optical system for imaging within a housing suitable for handheld operation, a controller 2 for controlling the camera 1, a observation monitor 3, a display monitor 4, and external devices such as a filing device 5 and a video printer 6.

Figure 2:
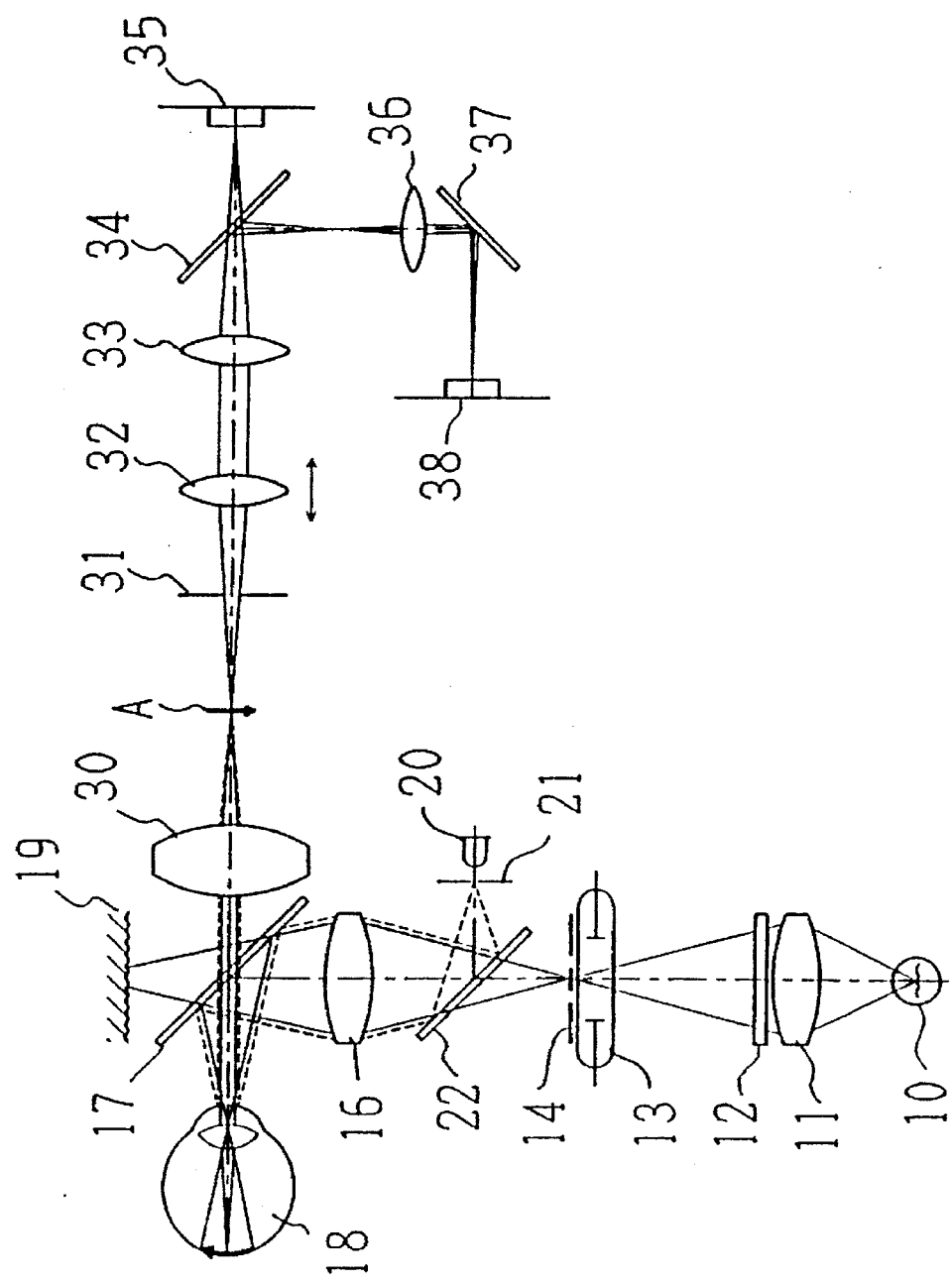
FIG. 2 shows a schematic side view of optical system incorporated in a camera of the embodiment according to the present invention.

The optical system of the camera 1 will be now explained. FIG. 2 shows a schematic side view diagram of the optical system disposed in the camera 1, of which illumination optical system, alignment index projection optical system, and observation/photographing optical system will be described separately.

(Illumination optical system)

Reference numeral 10 designates a halogen lamp, the light source for observation. 11 is a condensing lens, 12 is an IR (infrared) filter, which blocks visible light to make observation illumination invisible. 13 is a flash lamp for shooting photo-images. 14 is a ring slit which is a circular aperture. 16 is a projection lens, 17 is a beam splitter permitting the illumination light axis and the observation/photographing light axis to be coaxial, and 18 is an eye to be examined. 19 is a black absorbent for absorbing illumination light having passed through the beam splitter 17 for preventing noise light useless for the observation/photographing optical system from penetrating.

The light bundle emitted from the halogen lamp 10 is converged by the condensing lens 11, selected for wavelength by the IR filter 12 to illuminate the ring slit 14. The illumination light bundle limited to the annular profile by the ring slit 14, then passes through an infrared splitter mirror 22 as described later and through the projection lens 16, to be attenuated and reflected one half amount of light by the beam splitter 17 to finally be directed to the eye being examined. The reflected light bundle from the beam splitter 17 focuses the image of the ring slit 14 in the vicinity of the iris of the eye 18 and diffuses to illuminate the fundus of the area equal to or slightly larger than the field to be imaged with invisible infrared light.

The light bundle emitted from the flash lamp 13 illuminates the ring slit 14 to be limited thereby. The light bundle through the ring slit 14 for photographing passes through the path identical to that of the light from the halogen lamp 10 to illuminate the fundus of the eye to be examined.

(Alignment index projection optical system)

Reference numeral 20 designates a index illuminating light source which may be comprised of infrared light emitting diodes. 21 is a index plate having a pin-hole aperture in the center thereof. 22 is an IR-reflectable visible light-transmittable mirror, which serves to pass visible light and the almost major part of the IR light of which wavelength selected by the IR filter 12, and to reflect part of the IR light emitted from the light source 20 (10% or less of IR light is reflected while 90% or more is passed through). This mirror 22 recombines the illumination light axis with the light axis of the alignment index projection optical system.

The light emitted by the light source 20 illuminates the index plate 21. The alignment light bundle emitted from the pin-hole aperture of the index plate 21 is recombined with the illumination light bundle passing through the ring slit 14 from the infrared splitter mirror 22, and is projected to the eye being examined through the beam splitter 17 by the projection lens 16. The alignment index projection optical system is disposed such that the emitted alignment light bundle is converted at the position of the about half of the corneal curvature radius from the corneal surface when the apparatus is positioned to a predetermined working distance from the eye being examined.

In the present embodiment, the light path of the alignment index projection optical system is provided to be shared with that of the illumination optical system. However, it may be shared with the light path of the observation/photographing optical system. That is, the infrared splitter mirror 22 may be provided along with the light path of the observation/photographing optical system to reflect the index light bundle of the index plate 21 emitted from the light source 20 onto the eye to be examined.

(Finder/photographing optical system)

Reference numeral 30 designates an imaging objective lens, 31 is an aperture positioned so as to conjugate with the pupil of the eye 18 via the movable lens 30. 32 is a focusing lens which is adjustable along with the direction of the light path by using a lens moving device (not shown) for adjusting in accordance with the refractive power of the examined eye. 33 is an image formation lens, 34 is a dichroic mirror with characteristics that it reflects IR light and passes most visible light, and 35 is imaging elements of a CCD camera for image formation which has visible light sensitivity. As the imaging elements 35 which may, depending on the selection of elements and the performance of a connected video amplifier, capture a trace of lights significantly weaker than in case of shooting photograph using a 35 mm film, allows the amount of emitting light of the flash lamp 13 to be decreased.

Reference numeral 36 designates a relay lens for extending the light path. 37 is a mirror for reversing mirrored images. 38 is imaging elements of a observation CCD camera which have sensitivity in the IR wavelengths.

The light bundle from the fundus of the examined eye illuminated by the illumination optical system emerges by passing through in the center of the light axis so as not to overlap the image of the ring slit 14 near the pupil. The light bundle emerged from the examined eye is attenuated to approximately ½ of the amount of light by the beam splitter 17, to form an inverted image plane at the point marked as "A" by the object lens 30, and then to pass the imaging aperture 31. As the imaging aperture 31 is conjugated with the pupil, the diameter of the imaging light bundle emerged from the subject eye 18 will be virtually determined by the imaging aperture 31 so as not to be overlapped with the image of the ring slit 14 of the illumination optical system.

The IR light bundle for observation after having passed the imaging aperture 31 is passed the focusing lens 32 and the image formation lens 33 and reflected by the dichroic mirror 34 to focus on the imaging elements 38 by the relay lens 36 to form an image of the fundus. The ocular fundus image will be displayed on the observation monitor 3.

The visible light from the fundus illuminated by the imaging illumination light bundle from the flash lamp 13 passes the focusing lens 32, the image formation lens 33, and the dichroic mirror 34 to focus on the imaging elements 35 of the photo-imaging CCD camera to form an image of the ocular fundus. The image captured by the imaging elements 35 will be displayed on the display monitor 4 as a still image.

Figure 3:
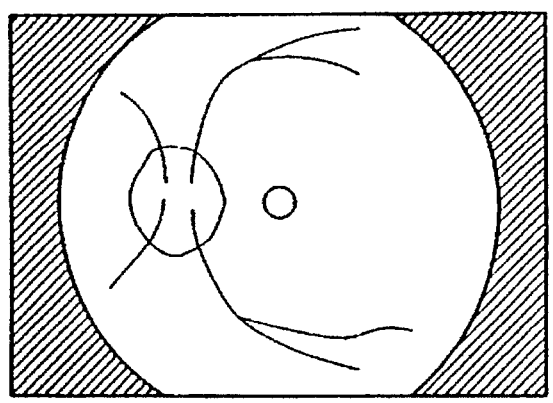
FIG. 3 shows an alignment index image displayed on a observation monitor together with a fundus image.

The alignment light bundle projected to the eye to be examined from the alignment index projection optical system, on the other hand, which is the light bundle on the center part by using the index plate 21, rather than the illumination light bundle with the center portion attenuated by the ring slit 14 of the illumination optical system, may form a index image by focusing on the position of about ½ of the corneal curvature radius from the corneal surface, together with the light from the ring slit when the apparatus is approximately disposed at its working distance from the eye to be examined. Since the position of the index image corresponds approximately to the position of the pupil, as well as matches approximately with the position of the ring slit image from the illumination optical system, this may be suitable for sharing the alignment index projection optical system with the illumination optical system. The alignment light bundle reflected from the cornea in such a condition may be almost parallel light bundle which directs to the objective lens 30. The reflection path thereafter may be the same as the light bundle for observation/photographing, and the light bundle may form an image on the imaging elements 38 similar to the IR light bundle for observation. On the observation monitor 3 an alignment index image will be displayed superimposed on the fundus image (see FIG. 3). As the index image is useful only when aligning, the light source 20 may be turned off when shooting photo-images if the index becomes obstructive.

In the observation/photographing optical system as described above, the imaging elements 35 and the imaging elements 38 may be interchangeable by replacing the dichroic mirror 34 with an IR-transmittable visible light-reflectable cold mirror, or by using a quick return mirror in place of the dichroic mirror.

Figure 4:
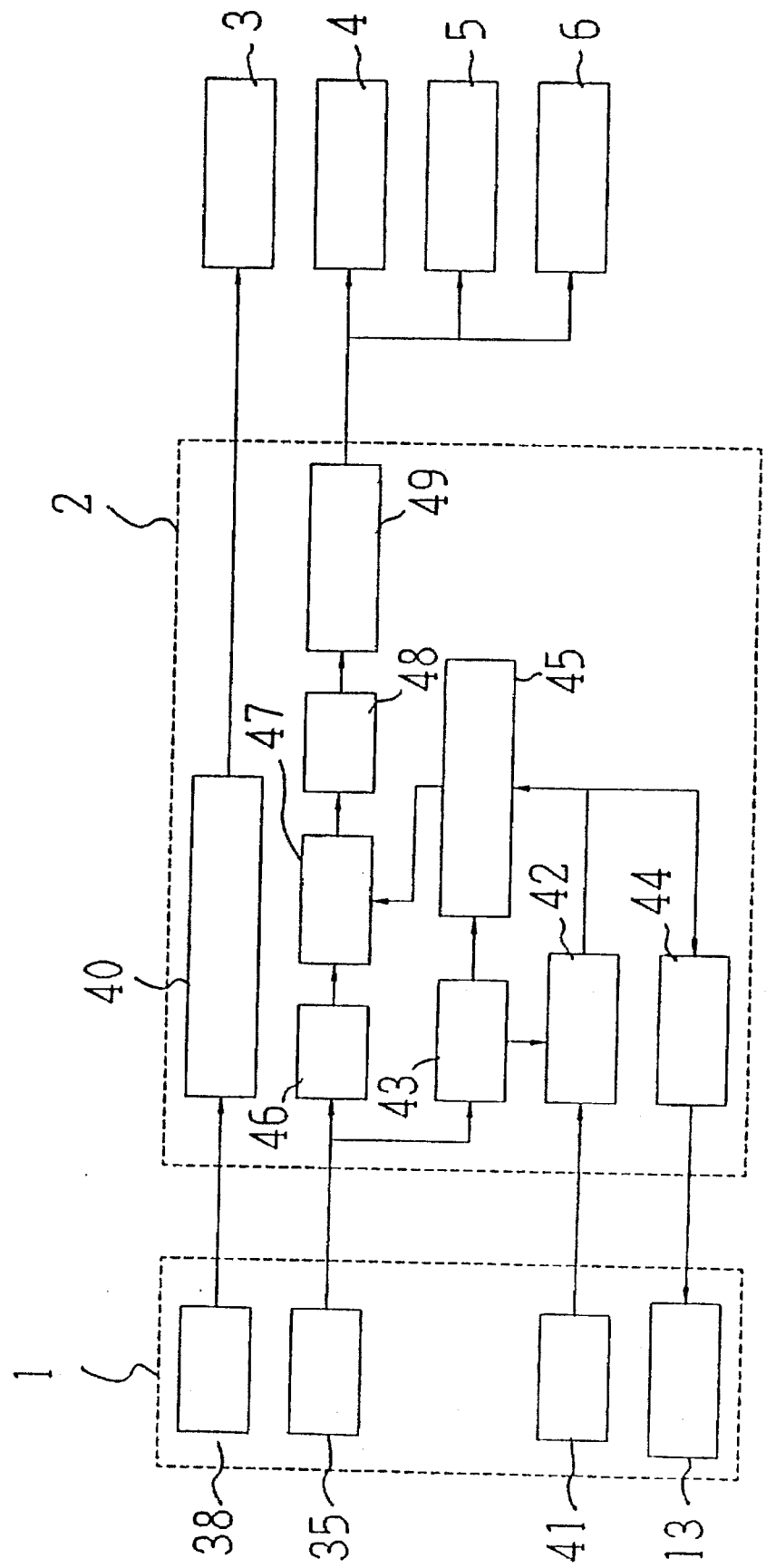
FIG. 4 shows a block diagram of the principal part of a signal processing system of the embodiment according to the present invention.

The operation of the apparatus having such architecture as described above will be described below with reference to the block diagram of the principal section of the signal processing system shown in FIG. 4.

Since the camera 1 enclosing the optical system is operable in a handheld manner, it may be used with any subject of examination in any position, such as lying patients, newborns and children, (experimental) animals, and handicapped persons. For the examination environment, ambient brightness may be preferably in a level capable of reading a newspaper at last, so as to open pupils widely in a natural mydriatic condition.

The operator turns on the halogen lamp 10 and the light source 20 to illuminate the eye to be examined by approaching in front thereof. The illumination light bundle of the halogen lamp 10 is so invisible by the IR filter 12, that the eye to be examined will be illuminated without load imposed. The reflected light bundle from the eye to be examined illuminated by the IR light bundle is captured by the imaging elements 38 of the IR-CCD camera, to cause the captured image to be displayed on the observation monitor 3 via a camera control circuit 40. The image of the eye to be examined observed on the observation monitor 3 will be initially the anterior of the eye, because photographing is performed by approaching the eye. The operator will adjust roughly the alignment horizontally and vertically so as to be able to observe the image of the anterior of the eye almost in the center of the field of view, and adjust the working distance of the apparatus as follows.

By approaching near the working distance of the apparatus (camela 1), a pupil image is enlarging on the observation monitor 3, and finally the fundus image will be displayed. In this condition the index image by the alignment index projection optical system may be confirmed on the observation monitor 3. Though the index image may be distended and unfocused at first, more the apparatus will approach the proper working distance, more the image will be sharpen and shrunken. The operator may adjust the working distance while holding the apparatus so as to position the index image on the center of the field of view, and the most appropriate working distance may be attained when the focus is best sharpen.

At the proper working distance, if the fundus image is out of focus due to the refractive power of the eye to be examined, then focus should be adjusted to the fundus by moving the focusing lens 32. Focusing may be structured by using any of known focusing indexs such as split line. Then the site to be photo-imaged will be decided in greater details, while maintaining the position of the index for detecting working distance image on the center of the field of view, by pivotally moving the apparatus about the pupil.

Once the fundoscopic site has been determined, the operator pushes down a photographing switch 41 on the camera 1. When the photographing switch 41 is pushed down, a trigger signal is generated to be transmitted to a timing circuit 42. The timing circuit 42 synchronize it with the synchronous signal of the imaging elements 35 inputted through a synchronous signal separator circuit 43 to transmit the trigger signal to a flash lamp driver circuit 44 and to an address control circuit 45. When the flash lamp 13 flashes by the flash lamp driver circuit 44, the imaging elements 35 captures fundus images which will be digitized in an A/D converter 46 to be stored in a frame memory 47 in synchronism with the signal from the address control circuit 45.

The image stored in the frame memory 47 will be converted to an analog signal by a D/A converter 48 to be transmitted through a video amplifier circuit 49 to the display monitor 4 to be displayed thereon instantaneously. The operator may determine whether or not the photo-image is in good condition by the displayed image. If the image is not good, then the photographing should be performed again by modifying, if necessary, the setting of the photographing conditions such as the amount of light of the flash lamp 13.

For storing the captured image, data is stored by operating the filing device 5. The image data stored in the filing device 5 may be retrievable, and unnecessary images may be deleted and edited. When a hard copy of images is needed to, for example, be appended to the patient's chart, hard copy printing may be obtained by operating the video printer 6.

The embodiment disclosed above may be modified, other than the modified aspects as described above, in various ways without departing from the technological spirits of the present invention. For example, the observation monitor 3 may be separated from other members such as the imaging elements. Also, a small LCD (liquid crystal display) device may be used for the observation monitor 3 to incorporate with the camera 1. Only the display monitor 4 may be provided by incorporating image switcher means for viewing thereon both images by switching images between the observation image and the photographic image, without providing separately the observation monitor 3 and the display monitor 4.

The forgoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the present invention and its practical application to enable one skilled in the art to utilize the present invention in various embodiments and with various modifications as are suited to the particular use contemplated. It is intended that the scope of the present invention be defined by the claims appended hereto, and their equivalents.

What is claimed is:

1. A fundus camera of hand-held type comprising:

first illumination optical system for illuminating an eye to be examined by using infrared light;

second illumination optical system for illuminating the eye to be examined by using visible light for photo-imaging, with part of light path being shared with that of said first illumination optical system;

an alignment index projection optical system for projecting an alignment index for the adjustment of working distance onto an cornea of the eye to be examined, wherein said alignment index projection optical system includes optical means for aligning coaxially its light axis with said first and second illumination optical system to share part of the light paths therewith;

an observation optical system having photoelectric imaging elements for observing the images of the focusing of said alignment index image and the fundus of the eye to be examined;

first display means for displaying images formed by the photoelectric imaging elements of said observation optical system;

a photographing optical system having photoelectric imaging elements for forming images of the fundus of the eye to be examined with part of light path being shared with that of said observation optical system; and a beam splitter disposed along with the light path shared by said photographing optical system and said observation optical system for reflecting the illumination light into the eye to be examined, wherein said beam splitter is disposed at the examinee's eye side opposite to an objective lens which is used in common with said observation optical system and said photographing optical system;

wherein suitability of alignment is determined by observing on said first display means the images of the focusing of said alignment index image formed through said beam splitter onto the photoelectric imaging elements of said observation optical system.

2. A fundus camera according to claim 1, wherein said alignment index projection optical system is provided with a light source for projecting an alignment index by using infrared light, said observation optical system imaging elements have sensitivity in the IR range, and the photoelectric imaging elements of said photographing optical system have sensitivity in the visible light range.

3. A fundus camera according to claim 1, further comprising second display means for displaying the fundus image by said photographing optical system.

4. A fundus camera according to claim 1, further comprising a handheld type enclosure.

5. A fundus camera according to claim 1, further comprising filing means for storing the fundus image data of the eye to be examined displayed on said first display means.

6. A fundus camera according to claim 5, further comprising printer means for printing out the fundus image data stored by said filing means.

* * * * *